United States Patent [19]

Fuchs et al.

[11] Patent Number: 5,646,277
[45] Date of Patent: Jul. 8, 1997

[54] PREPARATION OF CAOPROLACTAM

[75] Inventors: Eberhard Fuchs, Frankenthal; Tom Witzel, Ludwigshafen, both of Germany

[73] Assignee: BASF Aktiengellschaft, Ludwigshafen, Germany

[21] Appl. No.: 646,278

[22] PCT Filed: Nov. 15, 1994

[86] PCT No.: PCT/EP94/03782

§ 371 Date: May 16, 1996

§ 102(e) Date: May 16, 1996

[87] PCT Pub. No.: WO95/14665

PCT Pub. Date: Jun. 1, 1995

[30] Foreign Application Priority Data

Nov. 20, 1993 [DE] Germany .......................... 43 39 648.8

[51] Int. Cl.$^6$ ................................................. C07D 201/08
[52] U.S. Cl. ........................ 540/539; 540/451; 546/243; 548/553

[58] Field of Search ................................. 540/539

[56] References Cited

U.S. PATENT DOCUMENTS 2,301,964   11/1942   Martin .
4,625,023   11/1986   Mares et al. .
4,628,085   12/1986   Mares et al. .

FOREIGN PATENT DOCUMENTS 150 295    8/1985   European Pat. Off. .
2029540    10/1970  France .

Primary Examiner—Robert T. Bond
Attorney, Agent, or Firm—Keil & Weinkauf

[57] ABSTRACT

Cyclic lactams are prepared by reacting amino carbonitriles with water in liquid phase in a fixed bed reactor in the presence of heterogeneous catalysts which have no soluble constituents under the reaction conditions.

5 Claims, No Drawings

PREPARATION OF CAOPROLACTAM

The present invention relates to a novel process for preparing cyclic lactams by reacting amino carbonitriles with water in the presence of catalysts.

U.S. Pat. No. 4,628,085 discloses the reaction of 6-aminocapronitrile with water in the gas phase on acidic silica gel at 300° C. The reaction takes place quantitatively with an initial selectivity of 95% to produce caprolactam, but the productivity and selectivity are found to decline rapidly. A similar process is described in U.S. Pat. No. 4,625,023, in which a highly diluted gas stream composed of 6-aminocapronitrile, adiponitrile, ammonia, water and carrier gas is passed over a silica gel catalyst bed and a copper/chromium/barium/titanium oxide catalyst bed. Caprolactam is obtained with a selectivity of 91% and a conversion of 85%. In this case too there is rapid inactivation of the catalyst.

U.S. Pat. No. 2,301,964 relates to the uncatalyzed conversion of 6-aminocapronitrile to caprolactam in aqueous solution at 285° C. The yields are below 80%.

FR-A 2 029 540 describes a process for cyclization of 6-aminocapronitrile to caprolactam, using catalysts, which are metallic Zn or Cu powder, or oxides, hydroxides, halides, cyanides of rubidium, lead, mercury or elements with an atomic number of from 21 to 30 or 39 to 48. These catalysts are used as suspended catalysts in stirred autoclaves operated batchwise. Caprolactam is obtained in yields of up to 83%. However, there are problems in complete removal of the catalysts from the required caprolactam because the latter may form compounds with the soluble constituents of the metals used, or extremely fine particles may be produced by mechanical agitation.

It is an object of the present invention to provide a process for preparing cyclic lactams by reacting amino carbonitriles with water in the presence of catalysts which does not entail the disadvantages described above, provides high yields and selectivities and allows continuous operation.

It was furthermore intended to keep the amount of catalyst used as small as possible. In addition, it was intended to avoid the separation problems occurring in a suspension procedure, whether by complexation of the soluble constituents of the catalyst with components of the reaction mixture or due to extremely fine particles resulting from the high mechanical stress during agitation.

We have found that this object is achieved by carrying out the reaction in liquid phase in a fixed bed reactor in the presence of heterogeneous catalysts which have no soluble constituents under the reaction conditions. The heterogeneous catalysts are located in a fixed bed through which the reaction mixture flows continuously in a downward or upward direction.

Preferred embodiments of the process according to the invention are evident from the dependent claims.

The starting materials employed in the process according to the invention are amino carbonitriles, preferably those of the general formula I

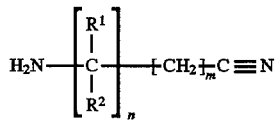

where n and m are each 0, 1, 2, 3, 4, 5, 6, 7, 8 or 9, and n+m total at least 3, preferably at least 4.

$R^1$ and $R^2$ can, in principle, be substituents of any type, it merely being necessary to ensure that the required cyclization is unaffected by the substituents. $R^1$ and $R^2$ are preferably, independently of one another, each $C_1$–$C_6$-alkyl, $C_5$–$C_7$-cycloalkyl or $C_6$–$C_{12}$-aryl.

Particularly preferred starting compounds are amino carbonitriles of the general formula

where m is 3, 4, 5 or 6, in particular 5. The starting compound when m=5 is 6-aminocapronitrile.

In the process according to the invention, the amino carbonitriles described above are reacted with water in liquid phase using heterogeneous catalysts to give cyclic lactams. Use of amino carbonitriles of the formula I results in the corresponding cyclic lactams of the formula II

where n, m, $R^1$ and $R^2$ have the abovementioned meanings. Particularly preferred lactams are those where n is 0 and m is 4, 5 or 6, in particular 5 (in the latter case, caprolactam is obtained).

The reaction is carried out in liquid phase at, in general, from 140° to 320° C., preferably 160° to 280° C.; the pressure is generally in the range from 1 to 250 bar, preferably from 5 to 150 bar, it being necessary to ensure that the reaction mixture is predominantly liquid under the conditions employed. The holdup times are generally in the range from 1 to 120, preferably 1 to 90 and, in particular, 1 to 60 min. In some cases, holdup times of 1–10 min have proved to be entirely sufficient.

In general, at least 0.01 mol, preferably 0.1–20 mol and, in particular, 1–5 mol of water are employed per mol of amino carbonitrile.

The amino carbonitrile is advantageously employed in the form of a 1–50% by weight, in particular 5–50% by weight, particularly preferably 5–30% by weight, solution in water (in which case the solvent is also reactant) or in water/solvent mixtures. Examples of solvents which may be mentioned are alkanols such as methanol, ethanol, n- and i-propanol, n-, i- and t-butanol and polyols such as diethylene glycol and tetraethylene glycol, hydrocarbons such as petroleum ether, benzene, toluene, xylene, lactams such as pyrrolidone or caprolactam, or alkyl-substituted lactams such as N-methylpyrrolidone, N-methylcaprolactam or N-ethylcaprolactam, as well as esters of carboxylic acids with, preferably, 1–8 carbon atoms. Ammonia can also be present in the reaction. Mixtures of organic solvents can, of course, also be used. Mixtures of water and alkanols in the water/alkanol ratio by weight of 1–75/25–99, preferably 1–50/50–99, have emerged in some cases as particularly advantageous.

It is, in principle, equally possible to employ the amino carbonitriles simultaneously as reactant and as solvent.

Examples of heterogeneous catalysts which can be used are: acidic, basic or amphoteric oxides of elements of the second, third or fourth main group of the Periodic Table, such as calcium oxide, magnesium oxide, boron oxide, aluminum oxide, tin oxide or silicon dioxide as pyrogenic silicon dioxide, as silica gel, kieselguhr, quartz or mixtures thereof, furthermore oxides of metals of the second to sixth subgroup of the Periodic Table, such as titanium oxide, amorphous, as anatase or rutile, zirconium oxide, zinc oxide, manganese oxide or mixtures thereof. It is likewise possible to use oxides of the lanthanides and actinides such as cerium oxide, thorium oxide, praseodymium oxide, samarium oxide, rare earth mixed oxide, or mixtures thereof with previously mentioned oxides. Examples of further possible catalysts are:

Vanadium oxide, niobium oxide, iron oxide, chromium oxide, molybdenum oxide, tungsten oxide or mixtures thereof. Mixtures of said oxides with one another are likewise possible. It is also possible to use some sulfides, selenides and tellurides such as zinc telluride, tin selenide, molybdenum sulfide, tungsten sulfide, sulfides of nickel, zinc and chromium.

The abovementioned compounds can be doped with or contain compounds of main groups 1 and 7 of the Periodic Table.

Further suitable catalysts are zeolites, phosphates and heteropolyacids, as well as acidic and alkaline ion exchangers.

These catalysts may in each case contain up to 50% by weight of copper, tin, zinc, manganese, iron, cobalt, nickel, ruthenium, palladium, platinum, silver or rhodium.

The catalysts may, depending on their composition, be used as unsupported or supported catalysts. Thus, for example, titanium dioxide can be used in the form of pellets or applied in the form of a thin layer to a support. Methods which can be used to apply $TiO_2$ to a support such as silicon dioxide, aluminum oxide or zirconium dioxide are all those described in the literature. Thus, a thin layer of $TiO_2$ can be applied by hydrolyzing organotitanium compounds such as titanium isopropoxide or titanium butoxide, or by hydrolyzing $TiCl_4$ or other inorganic Ti-containing compounds. Sols containing titanium oxide can also be used.

The advantage of the fixed bed procedure according to the invention is, on the one hand, the possibility of carrying out the cyclization continuously in a straightforward manner. On the other hand, surprisingly, the yields and selectivities achieved in the fixed bed are very high and thus permit short holdup times with very high throughputs. Since findings to date indicate that the catalysts have a long useful life, the amount of catalyst used is extremely low. The separation problems occurring in the suspension procedure, whether by complexation of the soluble constituents of the catalyst with components of the reaction mixture or due to extremely fine particles resulting from the high mechanical stress during agitation are completely eliminated in the continuously operated fixed bed procedure.

EXAMPLES

A solution of 6-aminocapronitrile (ACN) in water and ethanol in the ratios by weight stated in the table was passed under 100 bar into a heated tubular reactor with a capacity of 25 ml (diameter 6 mm, length 800 mm) which was packed with titanium dioxide (anatase) in the form of 1.5 mm pellets. The product stream leaving the reactor was analyzed by gas chromatography and high-pressure liquid chromatography (HPLC). The results are likewise to be found in the table.

TABLE

| Ex. | ACN [% by wt.] | Water [% by wt.] | $ACN/H_2O$ molar ratio [%] | Ethanol [% by wt.] | Temp. [°C.] | Holdup time [min] | Conversion [%] | Sel. [%] |
|---|---|---|---|---|---|---|---|---|
| 1 | 10 | 6.4 | 1:4 | 83.6 | 180 | 30 | 90 | 98 |
| 2 | 10 | 6.4 | 1:4 | 83.6 | 200 | 30 | 100 | 88 |
| 3 | 10 | 6.4 | 1:4 | 83.6 | 220 | 30 | 100 | 94 |
| 4 | 10 | 6.4 | 1:4 | 83.6 | 240 | 30 | 100 | 88 |
| 5 | 10 | 9.6 | 1:4 | 75.4 | 220 | 30 | 100 | 86 |
| 6 | 10 | 1.6 | 1:1 | 88.4 | 220 | 30 | 99 | 93 |

Comparative Test

A solution of 10% aminocapronitrile, 6.4% water and 83.6% ethanol was reacted as in the tests described in Example 1 without a heterogeneous catalyst at 250° C. with a holdup time of 30 min in an empty tubular reactor. The conversion was 28% and the selectivity for caprolactam was 74%.

EXAMPLES 7 to 16

Examples 7 to 16 were carried out as in Examples 1 to 6 using the same tubular reactor and employing 13.3 g of $TiO_2$.

TABLE

| Ex. | Cat. | Solvent | Temp. [°C.] | Water/ACN [mol/mol] | Feed rate [ml/h] | Free volume [ml] | HUT [min] | Conv. [%] | Sel. [%] |
|---|---|---|---|---|---|---|---|---|---|
| 7 | $TiO_2$ | EtOH | 180 | 2 | 9,3 | 9,3 | 60 | 96 | 92 |
| 8 | $TiO_2$ | EtOH | 230 | 2 | 62 | 9,3 | 9 | 100 | 91 |
| 9 | $TiO_2$ | EtOH | 260 | 2 | 139,5 | 9,3 | 4 | 99 | 91 |
| 10 | $TiO_2$ | EtOH | 180 | 4 | 9,3 | 9,3 | 60 | 98 | 93 |
| 11 | $TiO_2$ | EtOH | 230 | 4 | 80 | 9,3 | 7 | 92 | 94 |
| 12 | $TiO_2$ | EtOH | 230 | 4 | 56 | 9,3 | 10 | 100 | 90 |
| 13 | $TiO_2$ | EtOH | 260 | 4 | 139,5 | 9,3 | 4 | 98 | 91 |
| 14 | $TiO_2$ | EtOH | 180 | 10 | 9,3 | 9,3 | 60 | 98 | 91 |
| 15 | $TiO_2$ | EtOH | 230 | 10 | 56 | 9,3 | 10 | 97 | 93 |
| 16 | $TiO_2$ | EtOH | 260 | 10 | 62 | 9,3 | 9 | 100 | 93 |

EXAMPLES 17 to 22

Examples 17 to 22 were carried out as in Examples 1 to 6 using the same tubular reactor and employing 20 g of $TiO_2$.

TABLE

| Ex. | Cat. | Solvent | Temp. [°C.] | Water/ACN [mol/mol] | Feed rate [ml/h] | Free volume [ml] | HUT [min] | Conv. [%] | Sel. [%] |
|---|---|---|---|---|---|---|---|---|---|
| 17 | $TiO_2$ | MeOH | 220 | 2 | 29 | 14,2 | 30 | 100 | 91 |
| 18 | $TiO_2$ | EtOH | 220 | 2 | 29 | 14,2 | 30 | 100 | 89 |
| 19 | $TiO_2$ | n-PrOH | 220 | 2 | 29 | 14,2 | 30 | 100 | 79 |
| 20 | $TiO_2$ | i-PrOH | 220 | 2 | 29 | 14,2 | 30 | 100 | 87 |
| 21 | $TiO_2$ | n-BuOH | 220 | 2 | 29 | 14,2 | 30 | 100 | 81 |
| 22 | $TiO_2$ | TEG | 220 | 2 | 29 | 14,2 | 30 | 99 | 89 |

TEG = Tetraethylene glycol

EXAMPLES 23 to 27

Examples 23 to 27 were carried out as in Examples 1 to 6 using the same tubular reactor and employing different catalysts.

TABLE

| Ex. | Cat. | Solvent | Temp. [°C.] | Water/ACN [mol/mol] | Feed rate [ml/h] | Free volume [ml] | HUT [min] | Conv. [%] | Sel. [%] |
|---|---|---|---|---|---|---|---|---|---|
| 23 | $ZrO_2$ | EtOH | 220 | 2 | 27 | 13,3 | 30 | 90 | 83 |
| 24 | $\gamma$-$Al_2O_3$ | EtOH | 240 | 4 | 27 | 13,6 | 30 | 84 | 91 |
| 25 | $\gamma$-$Al_2O_3$ | EtOH | 260 | 4 | 27 | 13,6 | 30 | 97 | 93 |
| 26 | $\alpha$-$Al_2O_3$ | EtOH | 240 | 4 | 27 | 12,6 | 30 | 91 | 84 |
| 27 | $CeO_2$ | EtOH | 220 | 4 | 27 | 10,3 | 30 | 100 | 90 |

We claim:

1. A process for preparing cyclic lactams by reacting amino carbonitriles with water in the presence of catalysts, wherein the reaction is carried out in liquid phase in a fixed bed reactor in the presence of heterogeneous catalysts which have no soluble constituents under the reaction conditions.

2. A process as defined in claim 1, wherein the reaction is carried out at from 140° to 320° C.

3. A process as defined in claim 1, wherein amino carbonitriles of the formula

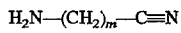

where
m is 3, 4, 5 or 6 are employed.

4. A process as defined in claim 3, wherein 6-aminocapronitrile is employed as amino carbonitrile.

5. A process as defined in claim 1, wherein a 1–50% by weight solution of the amino carbonitrile in water or in water/org. solvent mixtures is employed.

* * * * *